(12) United States Patent
Seo et al.

(10) Patent No.: US 12,070,275 B1
(45) Date of Patent: Aug. 27, 2024

(54) METHOD OF DESIGNING PATIENT-SPECIFIC GUIDANCE, AND PROGRAM AND SERVER THEREOF

(71) Applicant: SeeAnn Solution Co., Ltd., Incheon (KR)

(72) Inventors: Anna Seo, Incheon (KR); Youngjin Jeong, Incheon (KR); Hakjong Noh, Incheon (KR); Hyunho Ok, Incheon (KR)

(73) Assignee: SeeAnn Solution Co., Ltd., Incheon (KR)

( * ) Notice: Subject to any disclaimer, the term of this patent is extended or adjusted under 35 U.S.C. 154(b) by 0 days.

(21) Appl. No.: 18/416,546

(22) Filed: Jan. 18, 2024

(30) Foreign Application Priority Data

Jul. 12, 2023 (KR) .......... 10-2023-0090210

(51) Int. Cl.
  *A61B 34/10* (2016.01)
  *A61B 17/17* (2006.01)
  *G06F 30/20* (2020.01)
  *A61B 17/84* (2006.01)

(52) U.S. Cl.
  CPC .............. *A61B 34/10* (2016.02); *G06F 30/20* (2020.01); *A61B 17/846* (2013.01); *A61B 2034/102* (2016.02); *A61B 2034/105* (2016.02); *A61B 2034/107* (2016.02)

(58) Field of Classification Search
  CPC ........ A61B 2034/102; A61B 2034/105; A61B 2034/107; A61B 17/1778; A61B 17/1684; A61B 5/4576
  See application file for complete search history.

(56) References Cited

U.S. PATENT DOCUMENTS

| | | |
|---|---|---|
| 2015/0073424 A1 | 3/2015 | Couture et al. |
| 2019/0015221 A1 | 1/2019 | Neichel et al. |
| 2020/0179134 A1 | 6/2020 | Kelman et al. |

(Continued)

FOREIGN PATENT DOCUMENTS

| | | |
|---|---|---|
| KR | 10-2011-0087220 A | 8/2011 |
| KR | 10-2019-0025193 A | 3/2019 |
| KR | 10-2020-0117118 A | 10/2020 |

OTHER PUBLICATIONS

Signature one planner—Zimmer Biomet (Year: 2022).*

(Continued)

*Primary Examiner* — Samuel S Hanna

(74) *Attorney, Agent, or Firm* — Studebaker & Brackett PC

(57) ABSTRACT

Provided is a method of designing a guidance specific to a patient, including: specifying a first skeletal image plane in which a base plate is to be installed on a skeleton of a patient in which an affected area is located; displaying a normal vector N of the first skeletal image plane together with the skeleton of the patient in three dimensions (3D); displaying an intersection of the normal vector and the first skeletal image plane such that an operator arbitrarily moves the intersection or rotates the normal vector based on the intersection to determine a direction of a center pin; displaying a screen in which the base plate is installed according to a position (a center point) and direction of the center pin determined by the operator; and calculating a rotation angle and depth of peripheral screws to be installed on the base plate.

8 Claims, 21 Drawing Sheets

(56) References Cited

U.S. PATENT DOCUMENTS

2021/0093415 A1   4/2021   Moore et al.

OTHER PUBLICATIONS

Materialise Medical; "A Platform for Online 3D Planning and Ordering of 3D-printed Shoulder Guides"; Mar. 14, 2018; <URL: https://www.youtube.com/watch?v=3WT_4ya1Clw> See reproduction times 1:37 and 2:18.
Zimmer Biomet; "Signature ONE Planner User Guide"; 807.001 rev C; Issue Date Jan. 2022; pp. 1-20.
"Notice of Opinion Submission" Office Action issued in KR 10-2023-0090210; mailed by the Korean Intellectual Property Office on Oct. 27, 2023.
"Written Decision on Registration" Office Action issued in KR 10-2023-0090210; mailed by the Korean Intellectual Property Office on Jan. 3, 2024.

\* cited by examiner

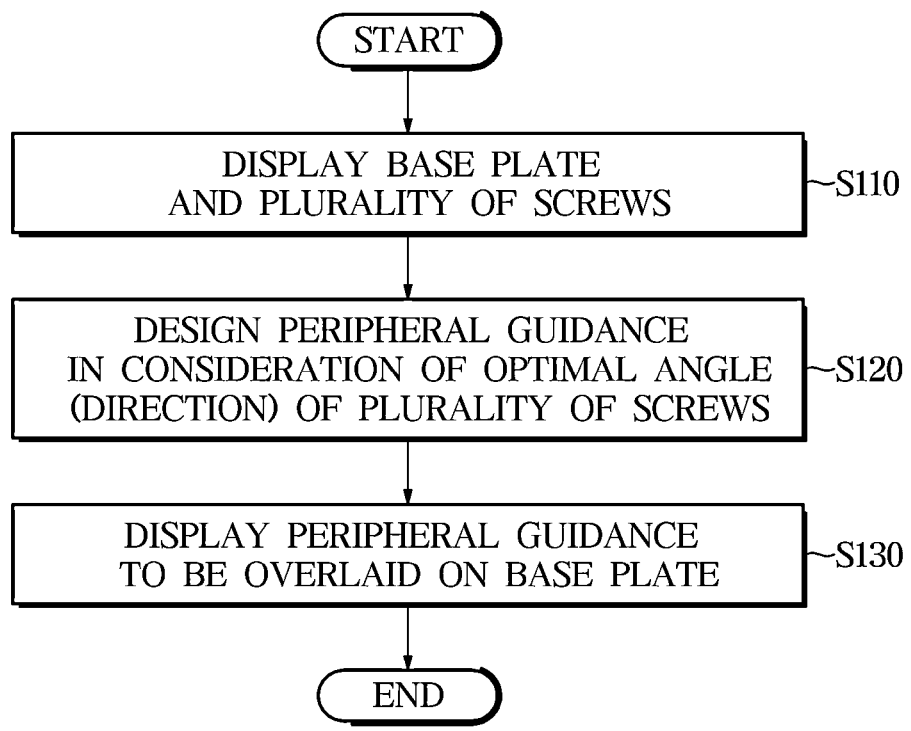

METHOD OF DESIGNING PATIENT-SPECIFIC GUIDANCE, AND PROGRAM AND SERVER THEREOF

CROSS-REFERENCE TO RELATED APPLICATION

This application claims priority to and the benefit of Korean Patent Application No. 10-2023-0090210, filed on Jul. 12, 2023, the disclosure of which is incorporated herein by reference in its entirety.

BACKGROUND

1. Field of the Invention

The disclosed technology relates to a method of designing a patient-specific guidance, and a program and server thereof, and more specifically, to a method of designing a patient-specific guidance for facilitating a secure fixation of an implant.

2. Discussion of Related Art

An artificial joint is a medical device designed to restore the original function of a joint, in which the joint cartilage is damaged, deformed, or fractured due to degenerative arthritis, age-related disease, autoimmune disease, trauma, or the like, by removing the joint and inserting an artificial prosthesis (an implant) into a joint plane and surroundings of the joint plane.

With an artificial joint replacement surgery, which is a process of inserting an artificial joint into the human body, it is possible to restore the normal function of the joint in the uncomfortable area. Typically, a shoulder artificial joint replacement surgery may be performed when the shoulder joint is damaged, conservative treatments are no longer effective, and there is severe pain.

However, since such surgeries have high risk and even minor errors may cause irreversible damage to the patient, it is important to accurately replace an artificial joint specific to each individual patient. This leads to an introduction of a surgery guidance that is designed based on each individual's different anatomy, and increases the accuracy of artificial joint placement. In other words, it is required to design a patient-specific surgical guidance used for an artificial joint replacement surgical implant in advance in a three-dimensional space. Therefore, today, a technology of establishing surgical plans based on patient's medical images (computed tomography: CT) and manufacturing a surgical guidance using 3D printing is advancing day by day.

In addition, since implantation methods vary depending on the surgeon performing the surgery, the present invention aims to provide a customized medical device that allows opinions of individual surgeons to be included in the guidance design. In this regard, reference may be made to the related art documents KR20200117118A or KR20110087220A.

SUMMARY OF THE INVENTION

The present invention is directed to providing a guidance in a virtual three-dimensional space that the guidance fixes an implant to be inserted in the most secure and accurate position in a virtual three-dimensional space.

In addition, the present invention is directed to designing the position, the angle, and the like in which a guidance may be inserted in the most accurate position, and providing a guidance that reflects an individual preference style preferred by each surgical surgeon.

The technical challenges that this embodiment aims to achieve are not limited to the technical challenges described above, and other technical challenges may be inferred from the following embodiments.

According to an aspect of the present invention, there is provided a method of designing a guidance specific to a patient, the method including: specifying a first skeletal image plane in which a base plate is to be installed on a skeleton of a patient in which an affected area is located; displaying a normal vector N of the first skeletal image plane together with the skeleton of the patient in three dimensions (3D); displaying an intersection of the normal vector and the first skeletal image plane such that an operator arbitrarily moves the intersection or rotates the normal vector based on the intersection to determine a direction of a center pin; displaying a screen in which the base plate is installed according to a position (a center point) and direction of the center pin determined by the operator; and calculating a rotation angle and depth of peripheral screws to be installed on the base plate.

The specifying of the first skeletal image plane in which the base plate is to be installed on the skeleton of the patient in which the affected area is located may include: calculating, when the operator selects at least four outermost points p1 to p4 on one side of the skeleton of the patient in which the base plate is to be installed, a center point that is a crossing point of the outermost points, or arbitrarily determining a center point; and calculating a normal vector from the center point.

The displaying of the intersection of the normal vector and the first skeletal image plane such that the operator arbitrarily moves the intersection or rotates the normal vector based on the intersection to determine the direction of the center pin may include: moving the center point in an arbitrary direction; or adjusting a rotation angle of the center pin.

The displaying of the screen in which the base plate is installed according to the position and direction of the center pin determined by the operator may include: displaying at least one base plate on a screen; and displaying a base plate selected by the operator among the at least one base plate to be overlaid on the first skeleton image plane in alignment with the center point.

The calculating of the rotation angle and the depth of peripheral screws to be installed on the base plate may include: specifying points p of the plurality of peripheral screws to be installed on the base plate; installing the plurality of peripheral screws in a same direction as the center pin at the specified points p of the plurality of peripheral screws; and rotating the plurality of peripheral screws in an arbitrary range of rotation angles at the specified points of the plurality of peripheral screws.

The rotating of the plurality of peripheral screws in the arbitrary rotation angle range at the specified points of the plurality of peripheral screws may include: calculating a distance d from the point of the peripheral screw to an intersection between a ray L in the same direction as the center pin and a triangle formed by arbitrary three points on the skeleton of the patient; repeatedly calculating the distance d with respect to a preset range of rotation angles ($r_x$, $r_y$) of the ray L; and determining a final rotation angle and depth of the peripheral screw based on the rotation angle ($r_x$, $r_y$) at which a maximum distance d is calculated from the repeatedly calculated distances.

The method may further include: generating a center pin guidance of the center pin generated with respect to the first skeleton image plane; and displaying the center pin guidance to be overlaid on the skeleton, or displaying only the center pin guidance.

The generating of the center pin guidance of the center pin generated with respect to the first skeleton image plane may include: setting, by the operator, a bridge position on the first skeletal image plane of the center pin; generating a bridge at the set bridge position; finally generating the center pin guidance including the bridge and displaying the finally generated center pin guidance.

The method may further include generating a peripheral screw guidance based on a rotation angle and depth of a peripheral screw to be installed on the base plate.

The generating of the peripheral screw guidance based on the rotation angle and depth of the peripheral screw to be installed on the base plate may include installing the peripheral screw guidance on an upper side of the base plate and displaying the installed peripheral screw guidance.

There is provided a computer readable recording medium on which a program for performing the method is recorded.

There is provided a server for designing a guidance specific to a patient, the server including: a memory and a processor, wherein the processor is configured to, in connection with the memory, specify a first skeletal image plane in which a base plate is to be installed on a skeleton of a patient in which an affected area is located; display a normal vector N of the first skeletal image plane together with the skeleton of the patient in three dimensions (3D); provide an operator with an intersection of the normal vector and the first skeletal image plane such that the operator arbitrarily moves the intersection or rotates the normal vector based on the intersection to determine a direction of a center pin; install the base plate according to a position (a center point) and the direction of the center pin determined by the operator; and calculate a rotation angle and depth of peripheral screws to be installed on the base plate.

The processor may be configured to: allow the operator to select at least four outermost points p1 to p4 on one side of the skeleton of the patient on which the base plate is to be installed; calculate a center point from a crossing point of the outermost points input from the operator; and calculate a normal vector from the center point.

The processor may be configured to receive, from the operator, an input to move the center point in an arbitrary direction or an input to change a rotation angle of the center pin.

The processor may be configured to further receive an input from the user other than the operator.

Specific details of other embodiments are included in the detailed description and drawings.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 6 is a flowchart for describing a method of designing a second guidance according to an embodiment.

DETAILED DESCRIPTION OF EXEMPLARY EMBODIMENTS

Figure 1:
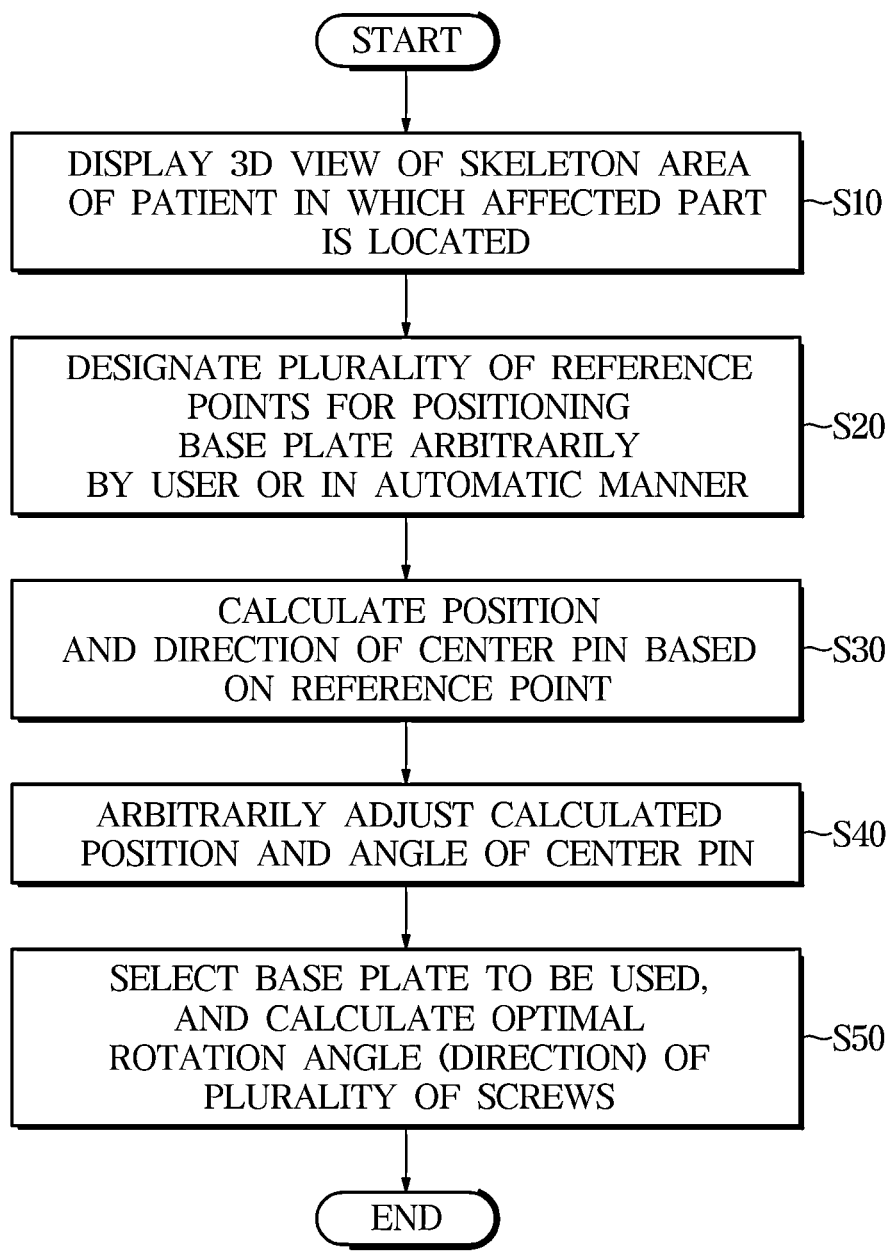
FIG. 1 is a flowchart providing an overview of a design method according to an embodiment.

Although terms used herein are selected from among general terms that are currently and widely used in consideration of functions in the exemplary embodiments, these may be changed according to intentions or customs of those skilled in the art or the advent of new technology. However, when a specified term is defined and used in an arbitrary sense, a meaning of the term will be described in the specification in detail. Accordingly, the terms used herein are not to be defined as simple names of the components but should be defined based on the actual meaning of the terms and the whole context throughout the present specification.

Throughout the specification, the term "comprises" or "includes" and/or "comprising" or "including" means that one or more other components may not be further excluded unless context dictates otherwise. In the specification, the term "part" or "module" refers to a unit for processing at least one function or operation that may be implemented in hardware, software, or a combination thereof.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

In the following description, terms such as "transmission," "communication," "sending," "reception," and other similar meanings of signals, messages, or information are not only meant to directly convey signals, messages, or information from one component to another. It also includes passing through other components.

In particular, "transmitting" or "sending" a signal, messages, or information to a component indicates the final destination of the signal, message, or information and does not mean a direct destination. The same is true for the "reception" of a signal or information. In addition, in this specification, that two or more pieces of data or information are "related" means that if one data (or information) is obtained, at least a portion of the other data (or information) may be obtained based thereon.

It should be understood that, although the terms "first," "second," "third," etc. may be used herein to describe various elements, these elements are not limited by these terms. These terms are only used for distinguishing one element from another.

For example, a first element could be termed a second element or a third element without departing from the scope of the present invention.

Although embodiments of the present disclosure will be described in detail with reference to the accompanying drawings in order to enable those skilled in the art to easily practice the disclosure, the present disclosure may be embodied in many different forms and should not be construed as being limited to the embodiments set forth herein.

Hereinafter, embodiments of the present invention will be described in detail with reference to the attached drawings.

FIG. 1 is a flowchart for describing a design method according to an embodiment. The method shown in FIG. 1 may be performed by an electronic apparatus 100 described with reference to FIG. 8. In FIG. 1, the method of designing a guidance is described as being divided into a plurality of operations, but at least some of the operations may be performed in a reverse order, performed in combination with other operations, omitted, further divided into a larger number of sub-operations, or combined into a smaller of operations. In addition, some operations described herein may be added.

A method of designing a guidance specific to a patient includes displaying, with respect to a skeleton of a patient to be subject to an artificial joint replacement, a three-dimensional (3D) view of a skeletal area of the patient in which an implant is to be installed (S10). In this case, as an example, the "patient's skeleton" may be specified as the glenoid around the scapula. Hereinafter, an area around the scapula is described as a specific embodiment of the patient's skeleton, but the disclosure is not limited thereto.

In this case, the 3D view displayed by the electronic apparatus 100 may display the skeleton in a transparent state or opaque state. In this case, when the skeleton is displayed transparently, the position of blood vessels located inside of the skeleton may be checked by a user. Additionally, the 3D view displayed by the electronic apparatus 100 may make clear distinction between cartilage and tibia. Accordingly, the electronic apparatus 100 may allow the positions of blood vessels in the skeleton to be clearly identified through a 3D view.

Figure 2:
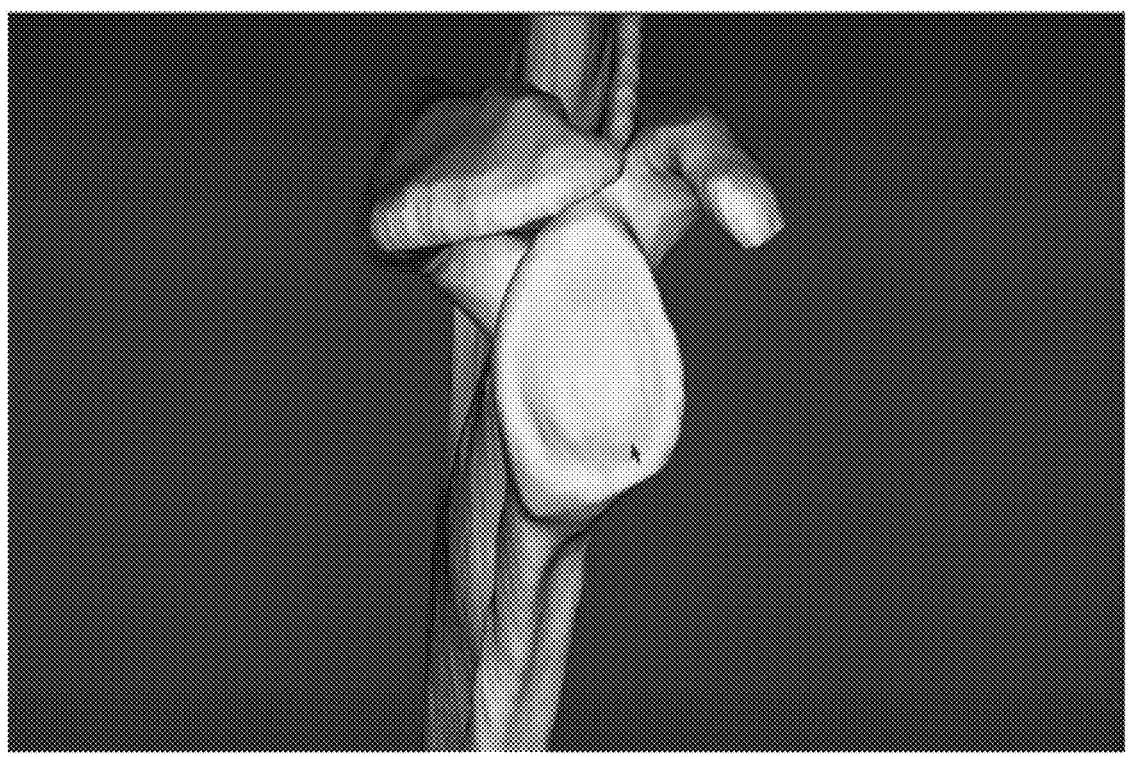
FIG. 2 shows a first skeletal image.

Hereinafter, a method of installing a base plate on a glenoid in the most secure manner is described with reference to FIGS. 2 and 3. FIG. 2 shows a first skeletal image in 3D. FIG. 2 shows a screen showing the glenoid facing forward, but the screen may be adjusted in all directions, forward, backward, leftward, and rightward directions, at 360 degrees, allowing the patient's skeletal area to be viewed.

Figure 3A:
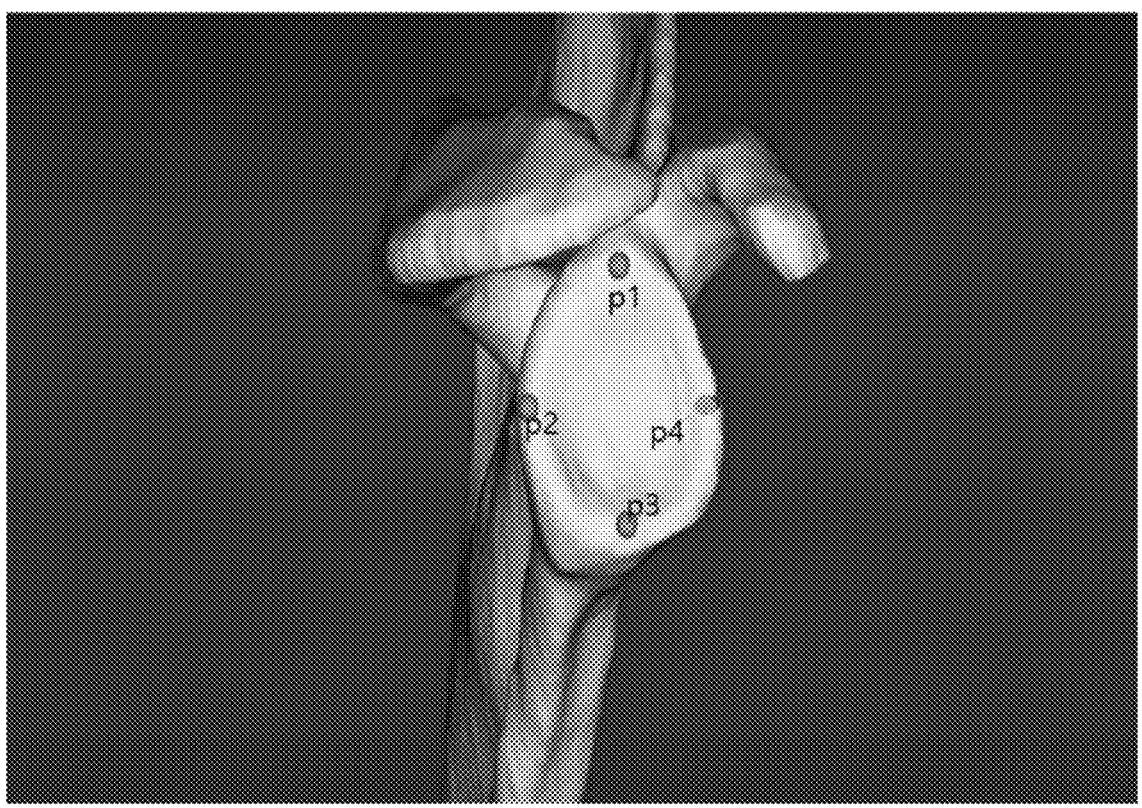
FIGS. 3A to 3J illustrate a process of calculating the angle of peripheral screws installed on a base plate in the first skeletal image.

Afterwards, the user designates a plurality of reference points for positioning a base plate arbitrarily by the user or automatically by a program (S20). Referring to FIG. 3A, the user may arbitrarily designate four points p1 to p4 on the outermost edge of the glenoid plane.

Figure 3B:
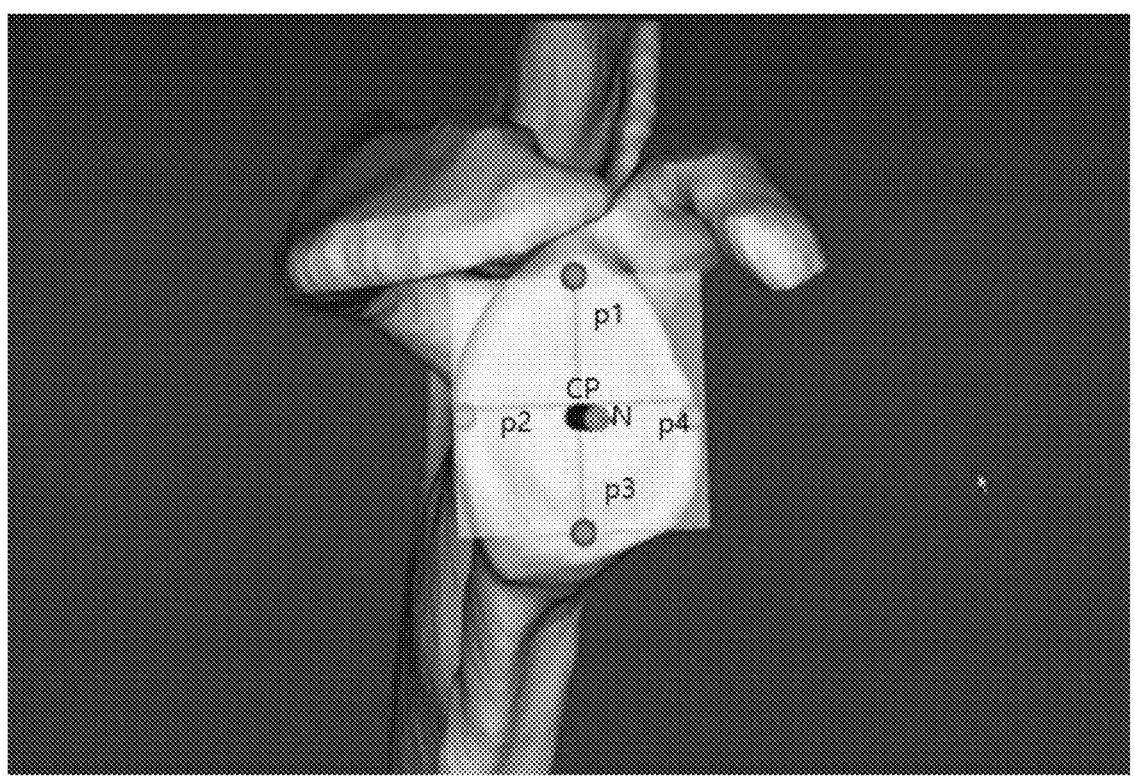

Afterwards, when the four points p1 to p4 are designated, the program according to an embodiment may calculate the position and direction of a center pin CP (S30 in FIG. 1 and FIG. 3B). In this case, the position of the center pin CP corresponds to a crossing point of a straight line $\overline{p_1, p_3}$ connecting P1 and P3 and a straight line $\overline{p_2, p_4}$ connecting P2 and P4, and the direction of the center pin CP is a normal vector N of a plane obtained by $\overline{p_1, p_3}$ and $\overline{p_2, p_4}$.. The normal vector is indicated by a red thick solid line.

However, the user may arbitrarily adjust the position of the generated center pin CP in forward, backward, leftward, and rightward directions on the glenoid plane.

Figure 3C:
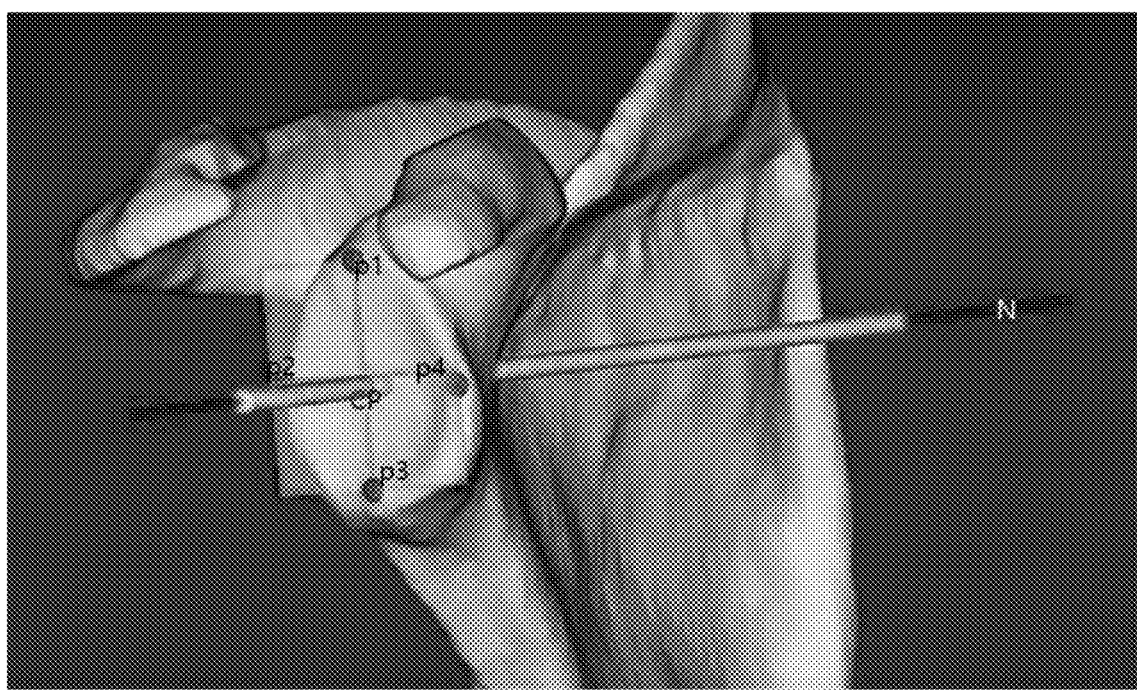
Figure 3D:

FIGS. 3C and 3D show the normal vector N of the center pin CP on a 3D screen, and the user may visually check whether the center pin of the scapula according to the embodiment is most deeply inserted into the scapula. That is, FIG. 3C is a screen showing the side and rear aspect of the scapula as seen from the back of the human body, and it can be visually confirmed that the normal vector N of the center pin CP is not directed toward a deep position of the scapula.

Figure 3E:
Figure 3F:
Figure 3G:
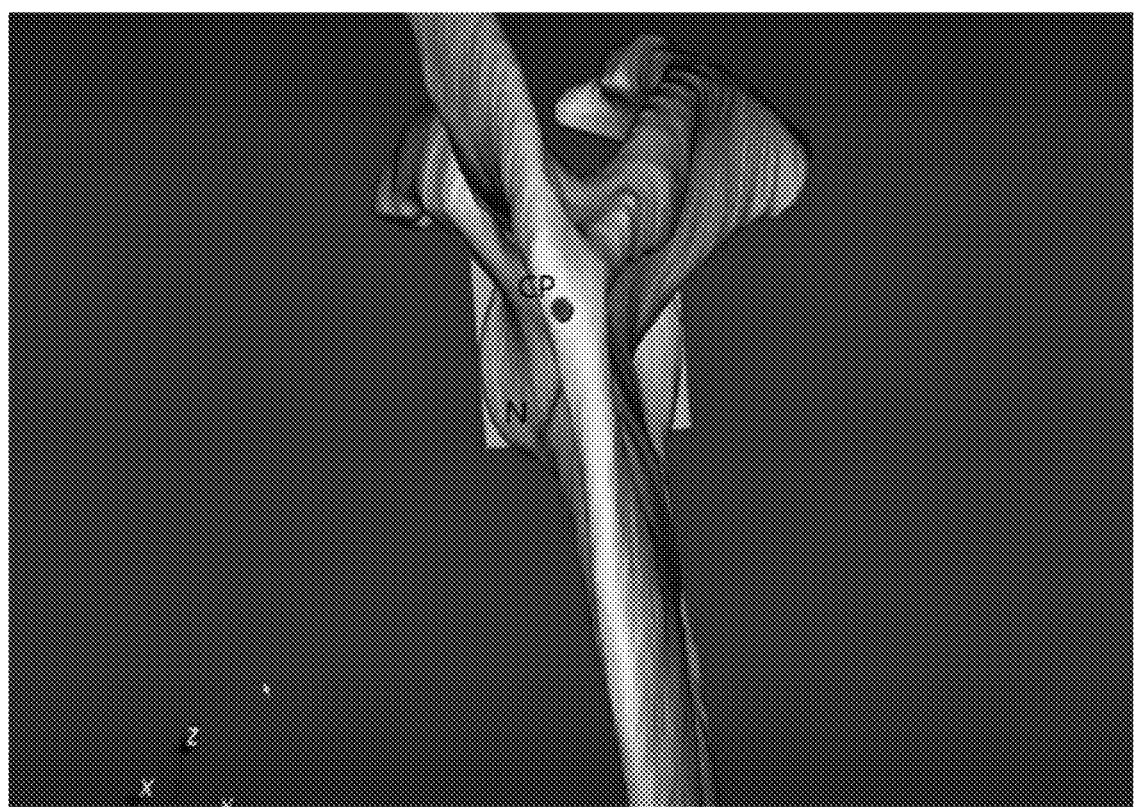

Therefore, when the center pin is positioned in the direction of the normal vector N, the center pin is not securely fixed, so there is a need to reposition the corresponding direction. That is, referring to FIG. 3D, it can be visually confirmed that adjusting direction of the normal vector N may allow for a more secure fixation of the center pin, as seen from the back of the glenoid of the scapula, that is, as seen from the inside of the scapula, Accordingly, FIGS. 3E and 3F are user-customized screens showing adjustment of direction of the center pin CP with respect to the normal vector N according to an embodiment.

According to an embodiment, the user may arbitrarily adjust the calculated position and angle of the center pin CP (S40 in FIG. 1). FIGS. 3E and 3F show rotation of the center pin CP in some direction from the normal vector N, moving the center pin CP toward the main axis of the scapula. Specifically, FIG. 3E is a screen in which the center pin CP from FIG. 3D is rotated about the x-axis direction, and thus is aligned in parallel with the most protruding part of the main axis of the scapula. Subsequently, FIG. 3F is a screen showing that the center pin CP rotated about the x-axis direction in FIG. 3E is rotated about the y-axis direction, and thus moved onto the main axis of the scapula.

However, although not shown, it is possible to perform axial movement on the position of the center pin CP. For example, the user may set a desired position moved relative to the center point of the center pin CP, which corresponds to the crossing point of the straight line $\overline{p_1, p_3}$ connecting P1 and P3 and the straight line $\overline{p_2, p_4}$ connecting P2 and P4, in each axis direction as a center point.

According to an embodiment, the user may check the 3D skeleton area displayed on the screen, visually confirm a position which is deep enough for the center pin CP to be most securely inserted, and select and determine the rotation angle of the center pin CP for each axis or the moving distance of the center pin CP.

In this case, the program may not only allow the user to arbitrarily adjust the direction and angle of the center pin CP, but also automatically move the center pin CP to the position in which the center pin CP may be most securely inserted in the scapula. Therefore, in FIG. 3G, it can be visually confirmed that the center pin CP is rotated to some degree about the x and y axes from the initial direction of the normal vector N and thus moved toward the deepest part of the scapula.

Figure 3H:
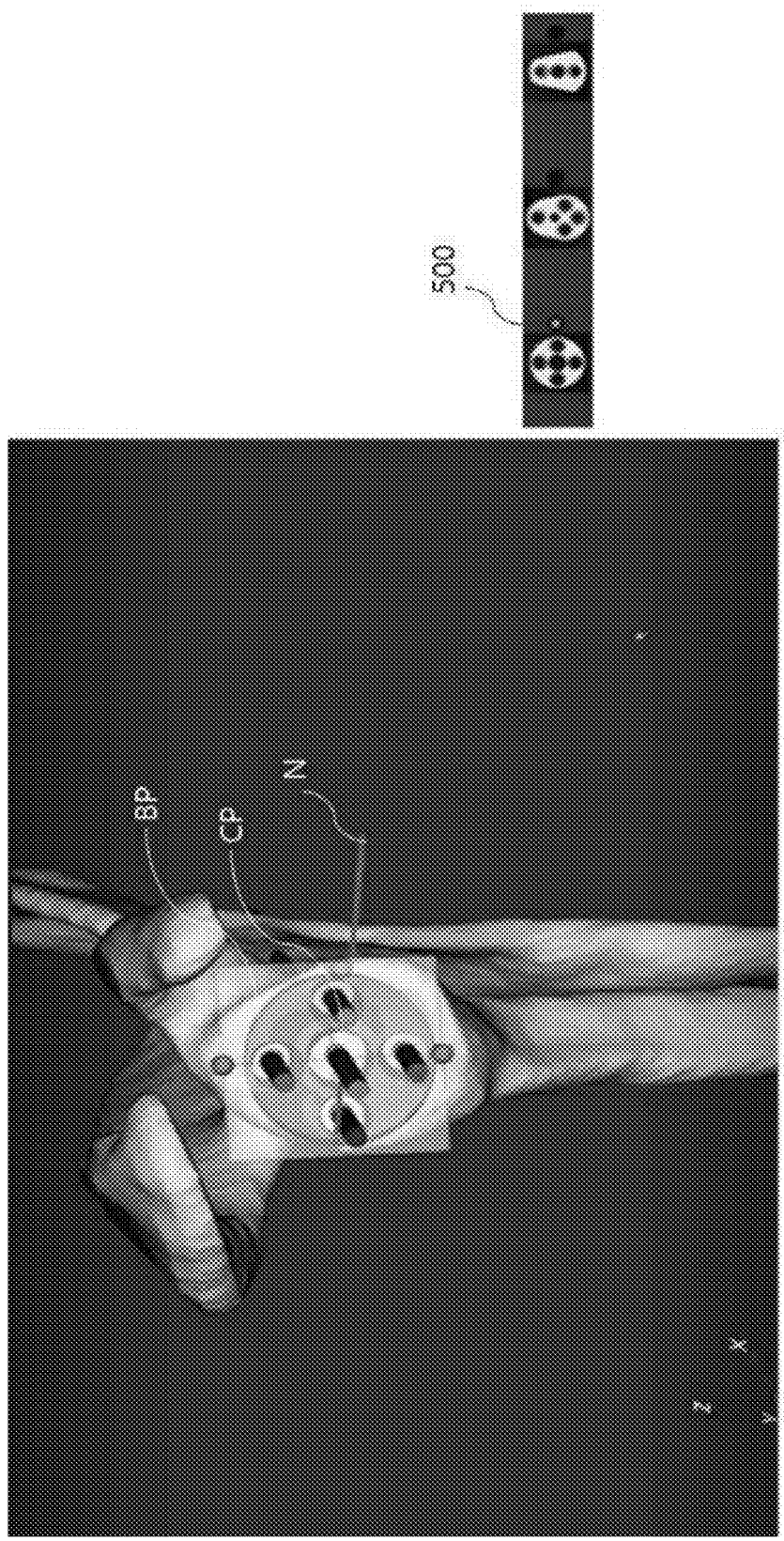

Afterwards, the program, once the direction of the center pin CP is determined, displays a base plate selection screen 500 on one side of the screen such that the user may select a base plate to be used. The base plate selection screen 500 may display a plurality of base plate shapes stored in the program. When the user selects a base plate to use from the base plate selection screen 500, the corresponding base plate BP is placed on the glenoid as shown in FIG. 3H.

Afterwards, the program calculates the optimal angle of each individual screw according to the number of screws to be used in the base plate BP (S50).

Figure 3I:
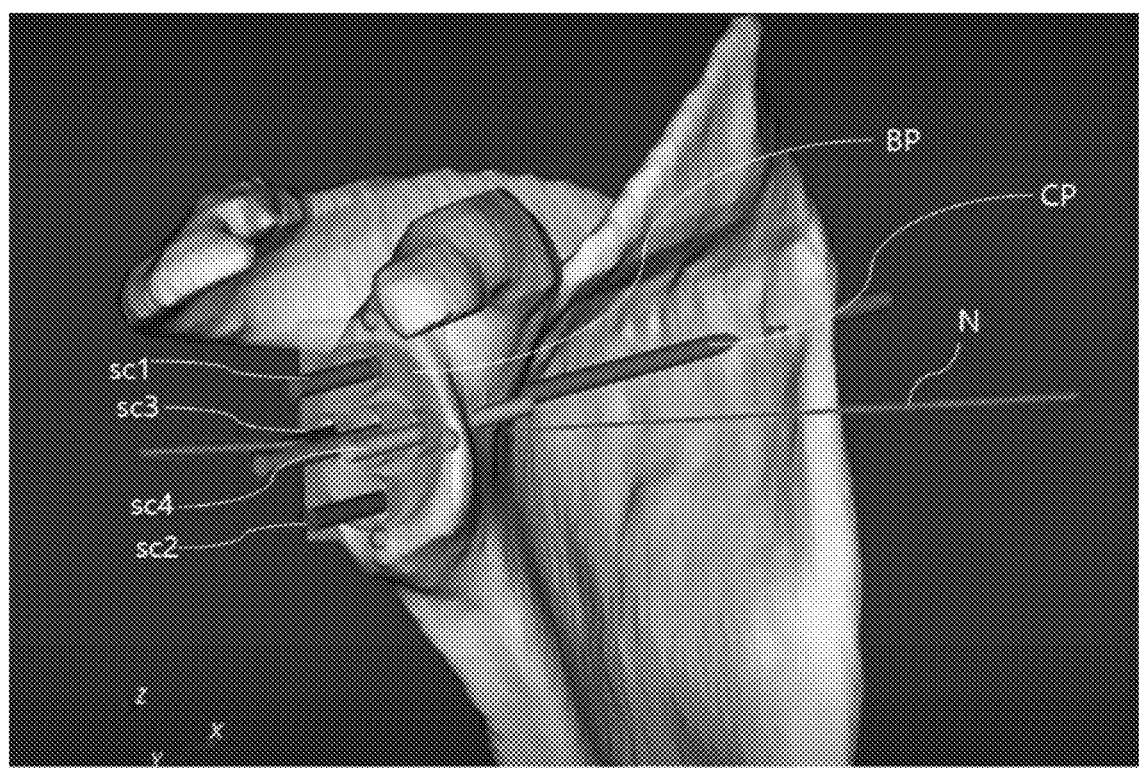
Figure 3J:
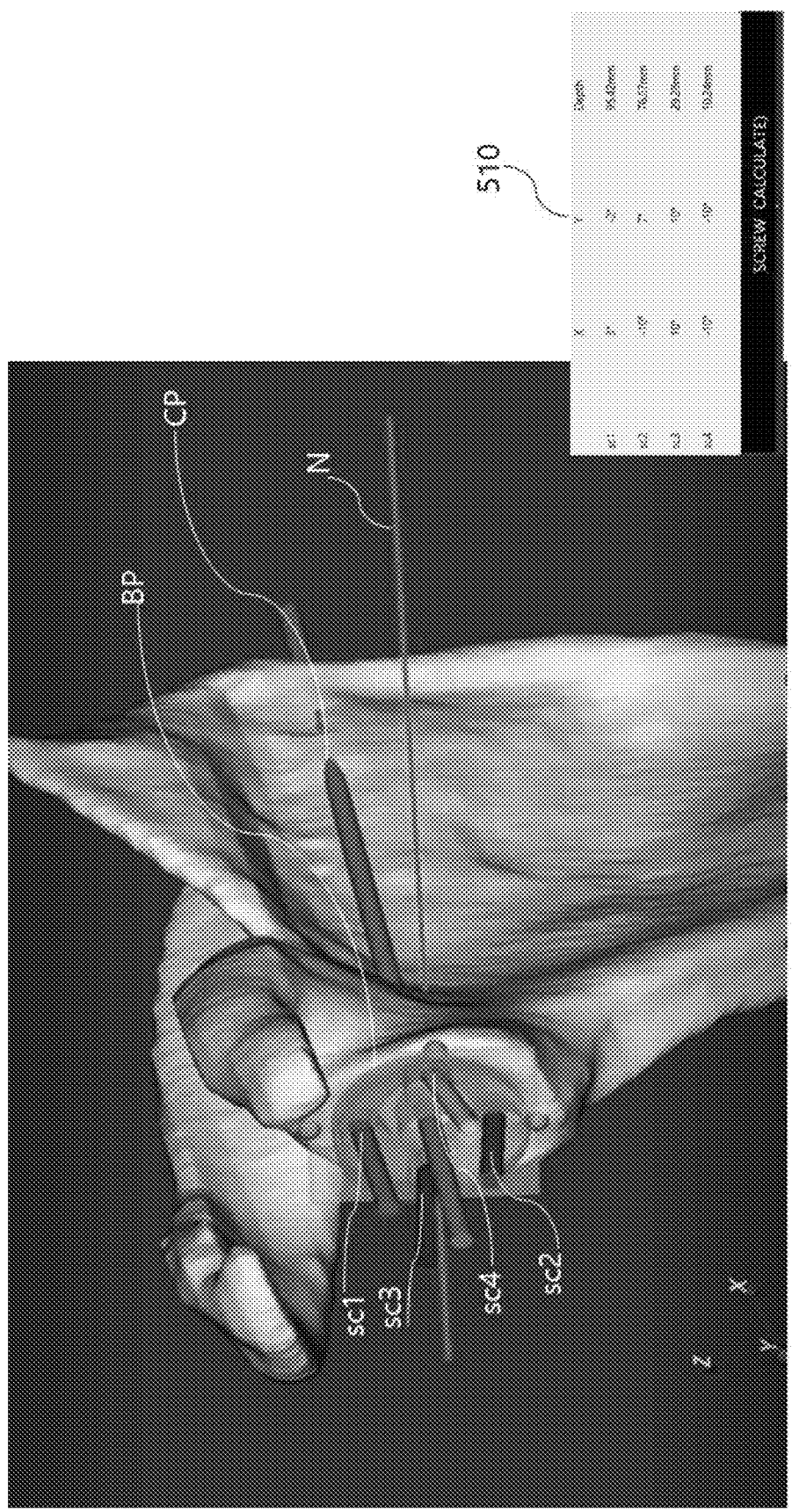

Specifically, FIG. 3I is a 3D screen showing screws including first to fourth screws sc1 to sc4 to fix the base plate BP, which is viewed from the side and rear aspect of the shoulder joint. Sequentially, FIG. 3J is a 3D screen after the angles of the plurality of screws to be used in the base plate are calculated. In FIG. 3J, a peripheral screw setting display unit 510 at the lower right side shows modified x and y axis rotation angles and depths of the first to fourth screws sc1 to sc4.

The angle of the peripheral screws according to the embodiment of the present invention may be calculated by repeating the following operations.

First, with the center point p of the center pin of the base plate BP, the mounting direction of the first to fourth screws sc1 to sc4 and the base plate are referred to as a normal vector N. In this case, the normal vector may be calculated through the operations described with reference to FIGS. 3A to 3B.

With respect to scapula 3D triangle mesh data M, the following operations are repeated to calculate the rotation angles of points p1 to p4 of the first to fourth screws sc1 to sc4. In this case, the scapula 3D triangle mesh data M is expressed as $M=\{t_1, t_2, t_3 \ldots t_{n-2}, t_{n-1}, t_n\}$, in which $t_n$ denotes a triangle, $t_n=\{p_{n1}, p_{n2}, p_{n3}\}$, $t_{L1n}=\overline{p_{n1}, p_{n2}}$, $t_{L2n}=\overline{p_{n2}, p_{n3}}$, and $t_{L3n}=\overline{p_{n3}, p_{n1}}$..

Operation 1: a ray L is emitted from each point p1 to p4 of the first to fourth screws in the direction of the normal vector N, to find a triangle crossing the ray L.

Operation 1-1: $n_{tj}$ denotes a normal vector of a triangle $t_j$, and $n_{tj}=t_{L1j} \times t_{L2j}$ (outer product)

Operation 1-2: when $N \cdot n_{tj}$ (inner product)≠0, an intersection $p_x$ of a plane containing the triangle $t_j$ and the ray L is calculated.

$$p_x = p_i + ((n_{tj} \cdot (p_{j1}-p_i))/(n_{tj} \cdot (p_y-p_i))) * (p_y-p_i) \quad \text{Equation1:}$$

In Equation 1, $p_y$ denotes any point on the ray L (for example, $p_y=p_i=2*N$).

Next, it is confirmed that the intersection $p_x$ is inside the triangle $t_j$ when a1 to a3 in Equations 2 to 4 below all have the same sign. However, without $p_x$ crossing the ray L, the process is repeated for another triangle.

$$a_1 = p_x \cdot t_{j1} \quad \text{Equation2:}$$

$$a_2 = p_x \cdot t_{j2} \quad \text{Equation3:}$$

$$a_3 = p_x \cdot t_{j3} \quad \text{Equation4:}$$

Operation 1-3: when the intersection $p_x$ having the same sign in Equation 2 to Equation 4, the distance d between $P_i$ and $P_x$, which is a crossing point $P_x$ with the ray L, is calculated.

Operation 2: with respect to $P_i$ ($P_1$ to $P_4$), the ray L is rotated about the x-axis from −15° to +15° in 1° increments, and for each rotation of 1° about the x-axis, the ray L is rotated about the Y-axis from −15° to +15° in 1° increments, and operations 1-1 to 1-3 are repeated for each rotation angle ($r_x$, $r_y$).

In this case, the rotation angle and depth of each peripheral screw for the maximum depth (d) value may be determined as max $\{d:r_x,r_y\}$, but when the determined rotation angle and depth of each peripheral screw are determined to be located in the cartilage, the program may readjust the corresponding depth and rotation angle such that the peripheral screw is located in the tibia. This is to resolve the issue of the peripheral screw not being securely fixed as being located in the cartilage.

In addition, in a case in which the rotation angle and depth of each peripheral screw are determined, when the determined rotation angle and depth include a position and depth at which the peripheral screw touches a nerve or blood vessel, the program may readjust the corresponding depth and rotation angle to ensure that the peripheral screw does not touch the nerve or blood vessel.

For example, when repeating operations 1-1 to 1-3 for the rotation angle ($r_x$, $r_y$) by rotating the ray L around the x-axis and y-axis in operation 2, the maximum depth (d) value is determined when the position of a depth (d) value at a rotation angle of each peripheral screw is located in the tibia.

In this case, information about an area in which the tibia and cartilage are distinguished is calculated in advance through an acquired skeletal image, and the disclosed method is implemented to distinguish the tibia and the cartilage in advance from the previously acquired skeletal image information, and thus the position of the final depth (d) value may be determined as described above.

In addition, although not described in detail, the program according to an embodiment may identify the position of nerves, blood vessels, and cartilage in the skeleton through the acquired 3D skeleton view such that the depth and rotation angle determined accordingly is arbitrarily modified and suggested.

Figure 4:
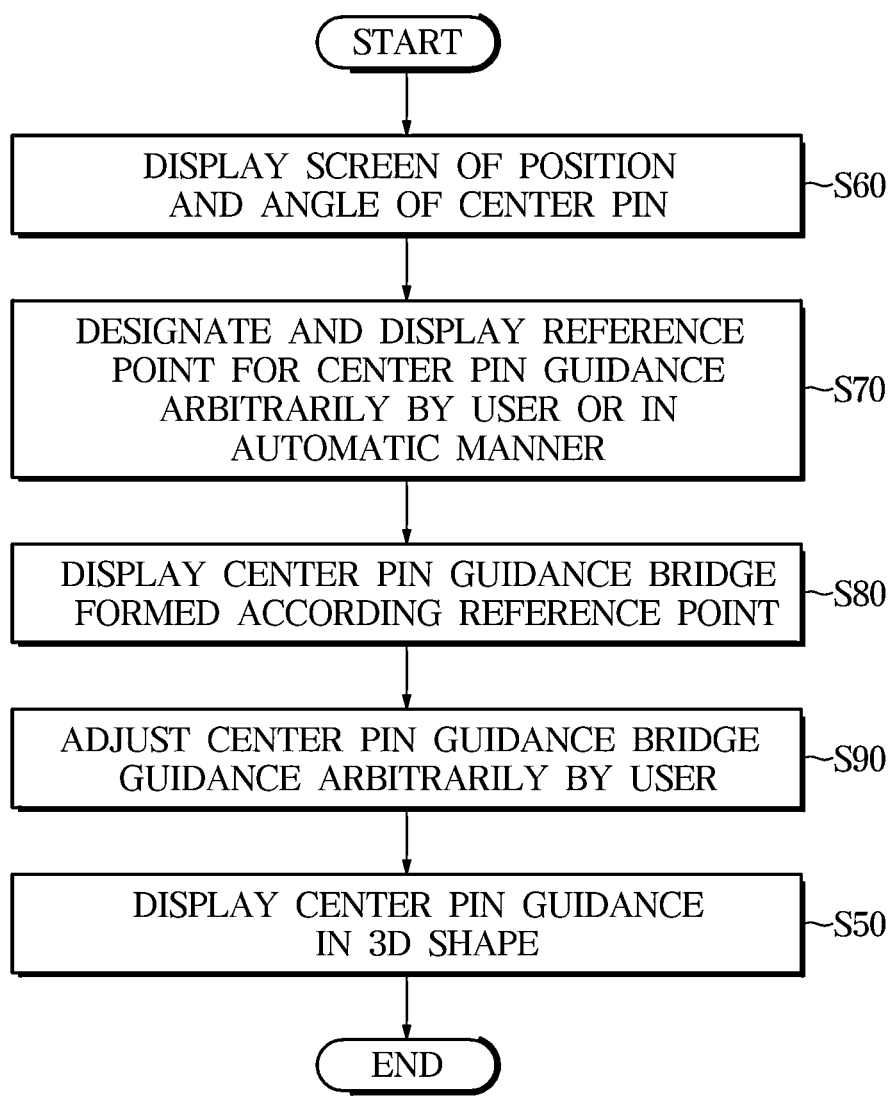
FIG. 4 is a flowchart for describing a method of designing a first guidance according to an embodiment.

FIG. 4 describes a method of generating a guidance bridge of the center pin CP according to an embodiment after calculating the angle of the peripheral screw in a peripheral screw screen portion of FIG. 3.

First, a screen of the position and angle of the center pin CP is displayed (S60). That is, as shown in FIG. 4A, it is possible to show the position in which the center pin CP is placed in the glenoid. In this case, the position and angle of the center pin CP are determined as described above with reference to FIGS. 2 and 3, and thus details thereof is omitted in the following description.

Figure 5A:
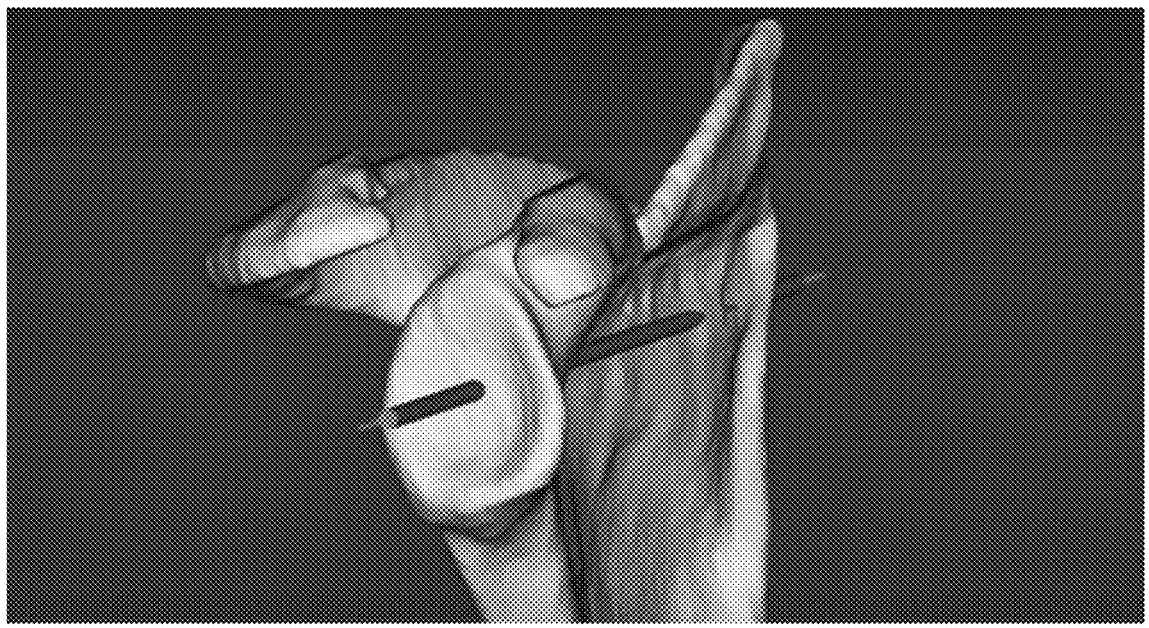
FIGS. 5A to 5F show a process of designing the first guidance.
Figure 5B:
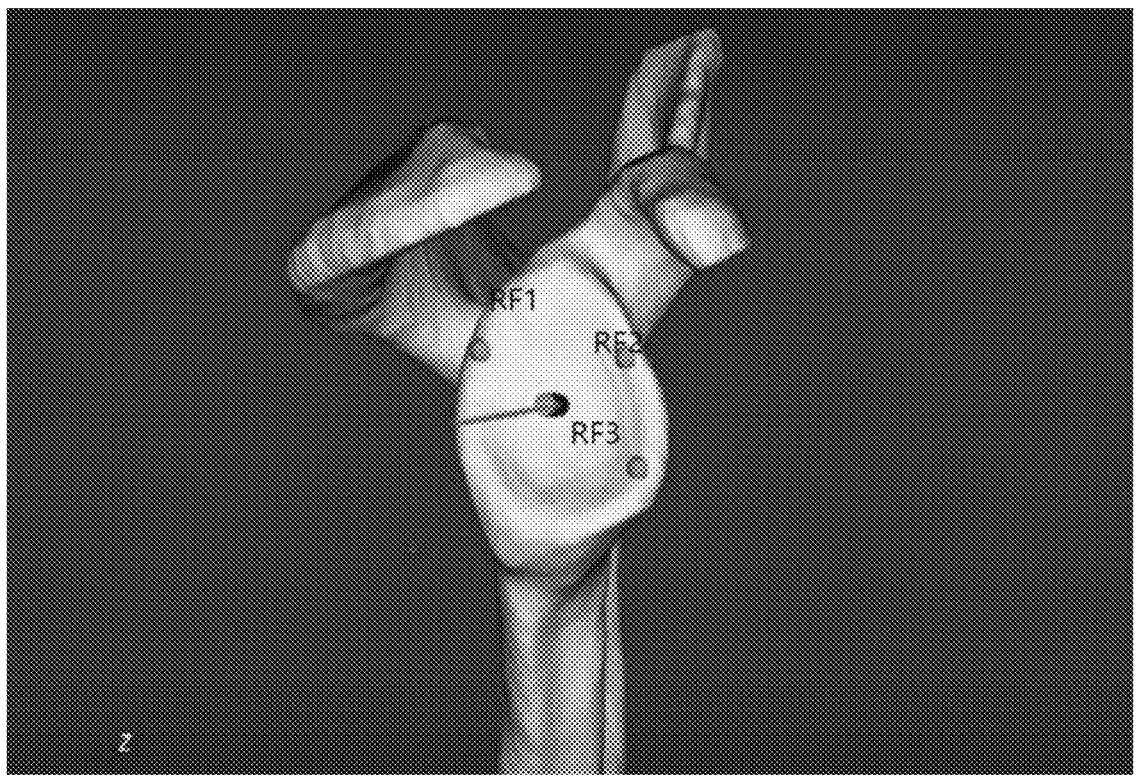
Figure 5C:
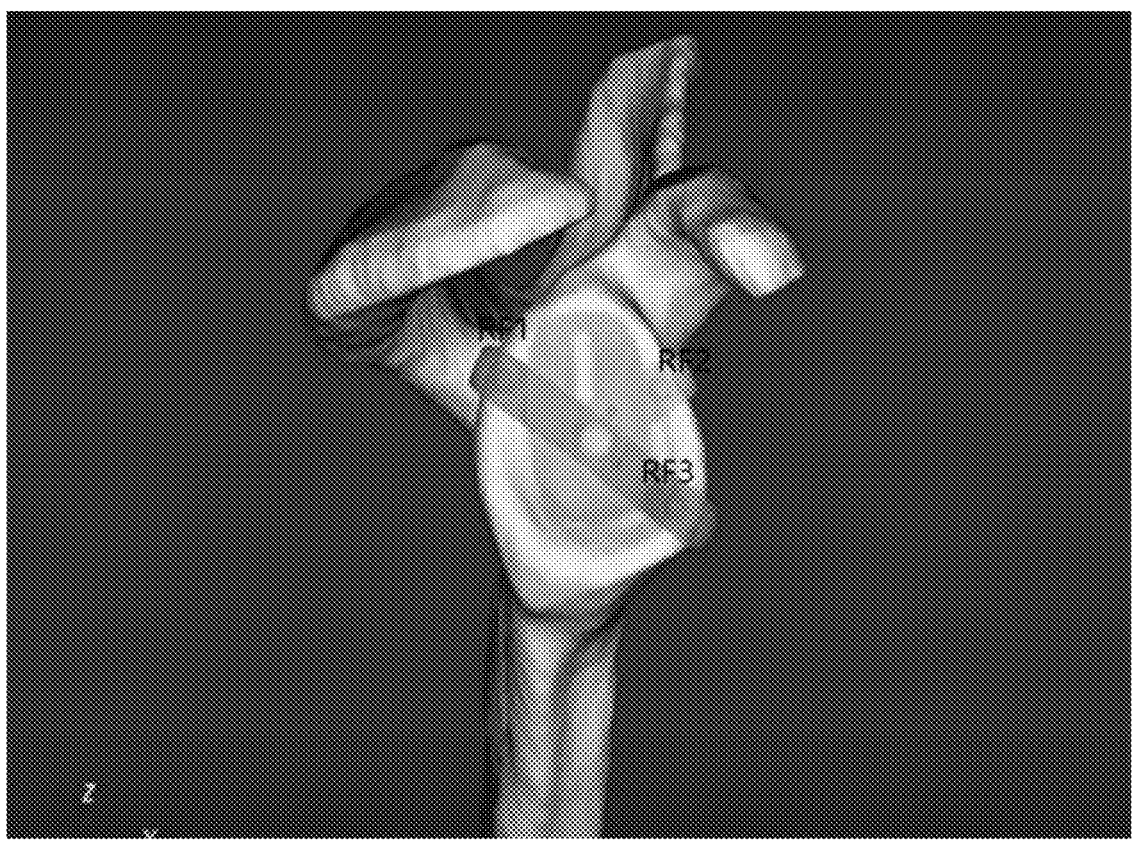

Afterwards, a reference point for a center pin guidance is designated arbitrarily by a user or in an automatic manner, and the designated reference point is displayed (S70). Specifically, a case in which the user arbitrarily designates a reference point RF of a center pin guidance may be shown in FIG. 5B.

When the user specifies reference points RF1 to RF3, a center pin guidance bridge is displayed such that center pin guidance bridge is installed at the reference point (S80). Although not shown, it is also possible for the user to specify the height, width, thickness, and the like of the center pin guidance bridge to be used.

Figure 5D:
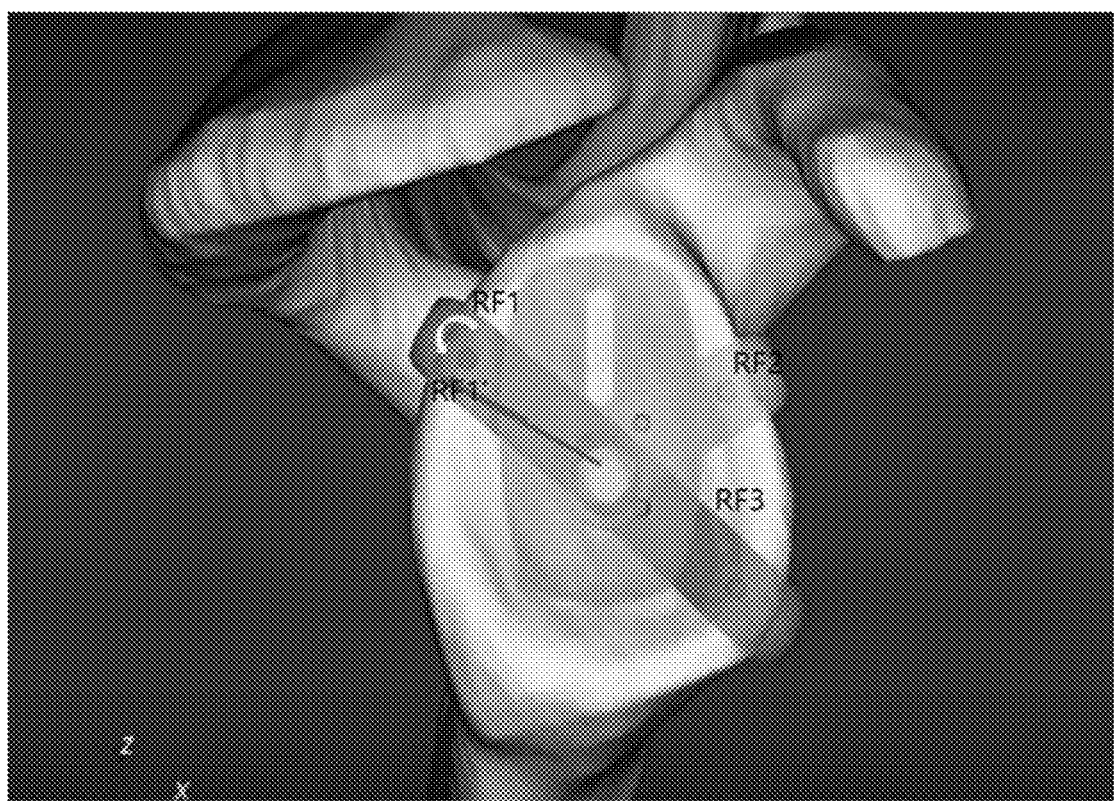
Figure 5E:
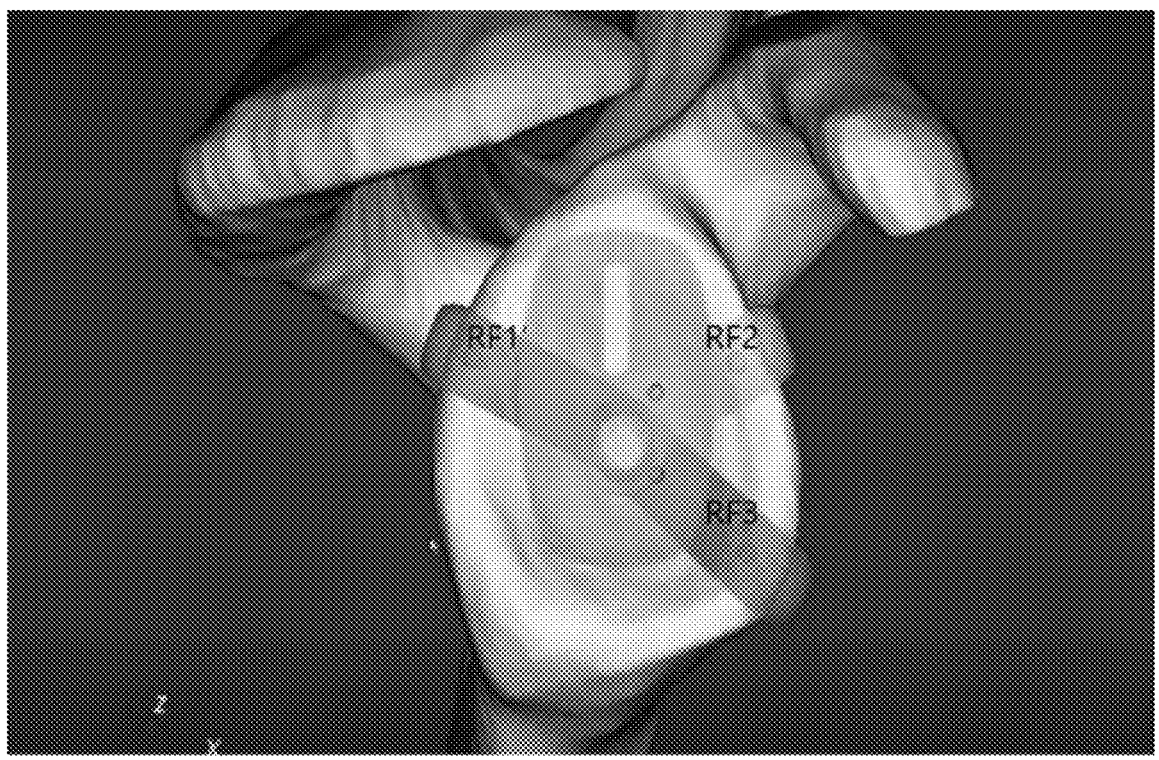
Figure 5F:
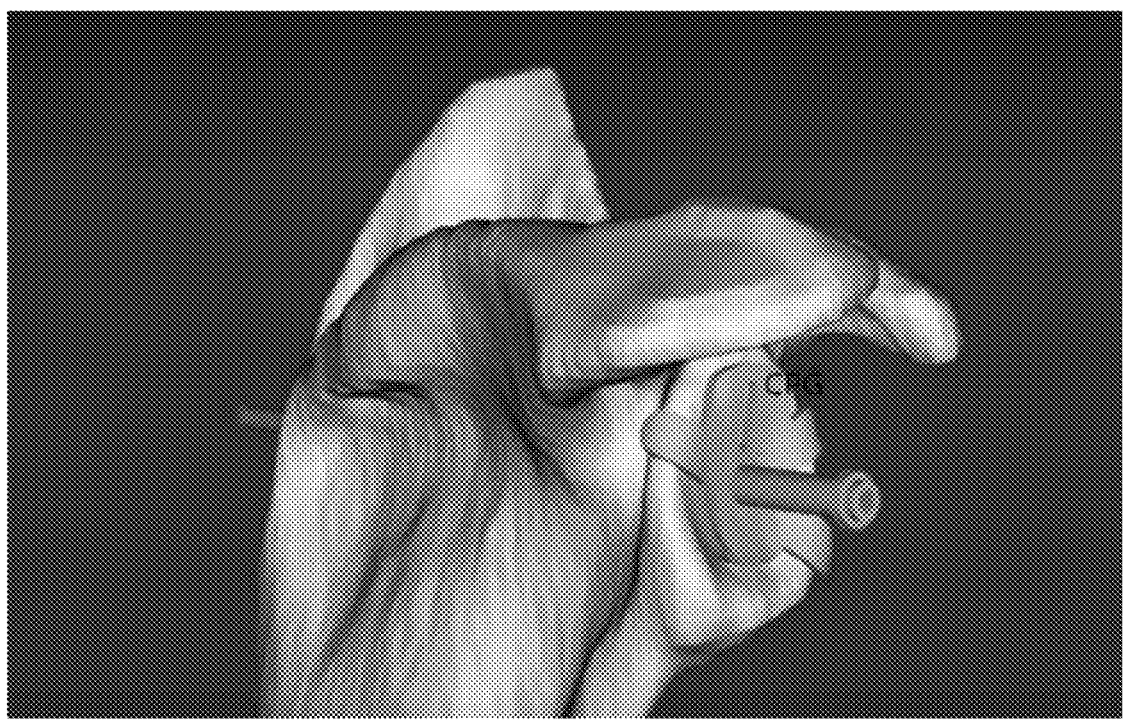

In addition, the user may partially adjust the positions of the reference points with respect to the center pin guidance bridge installed at the position of the designated reference points RF1 to RF3. In other words, the user may arbitrarily adjust the center pin guidance bridge (S90). For example, in FIG. 5D, it can be seen that the position of the first reference point RF1 may be rotated counterclockwise on the glenoid to a "first reference point RF1'" Therefore, in FIG. 5E, the final center pin guidance bridge is shown as a 3D shape, and the program according to an embodiment displays a 3D shape of the final center pin guidance CPG as shown in FIG. 5F (S100). In addition, although not shown, according to an embodiment, the user visually adjusts the transparency of the guidance, the center pin, the peripheral screws, the scapula, and the like for the user to easily select and display the 3D image of each individual component.

In the description above, a method of designing a guidance according to the first embodiment has been described. In particular, the guidance according to the first embodiment has been illustrated together with the method of designing the center pin guidance CPG with reference to FIGS. 5A to 5F.

Hereinafter, a method of designing a guidance according to the second is described. In particular, the guidance according to the second embodiment is illustrated together with a method of designing peripheral screws with reference to FIGS. 7A to 7C.

Figure 7A:
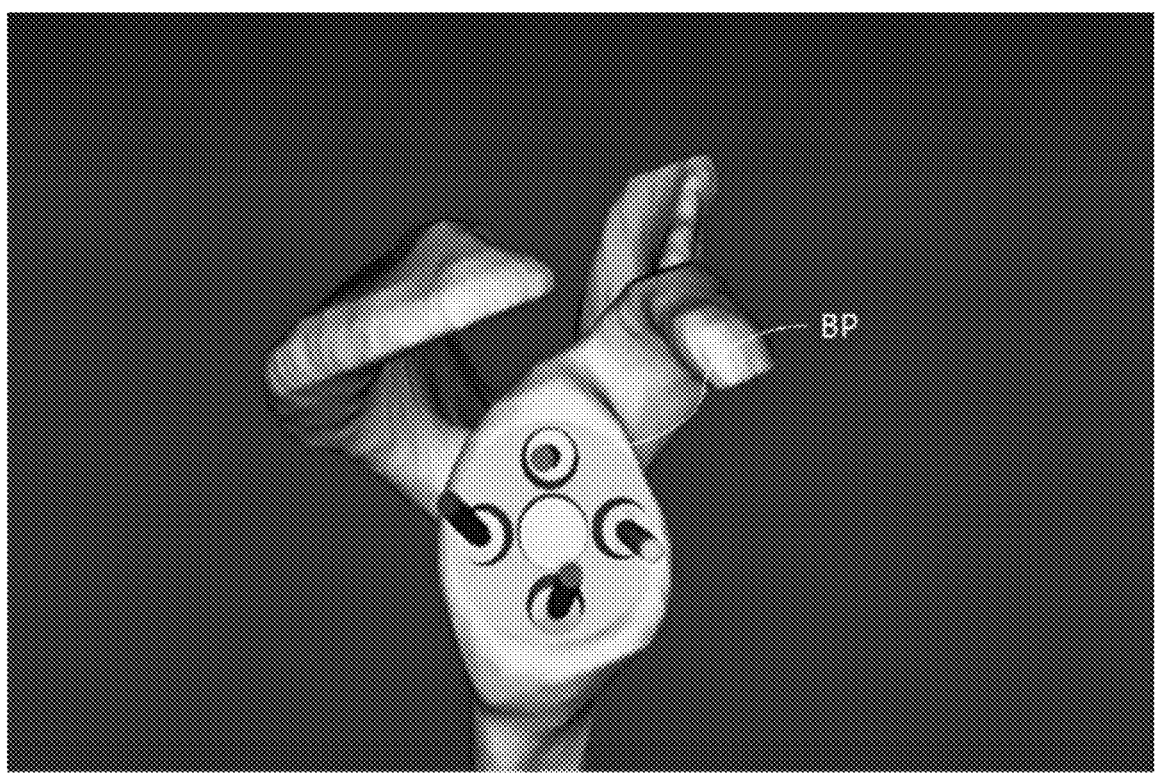
FIGS. 7A to 7B show a process of designing the second guidance.

FIG. 7A is a screen showing a base plate BP placed on a glenoid according to an embodiment.

Figure 7B:
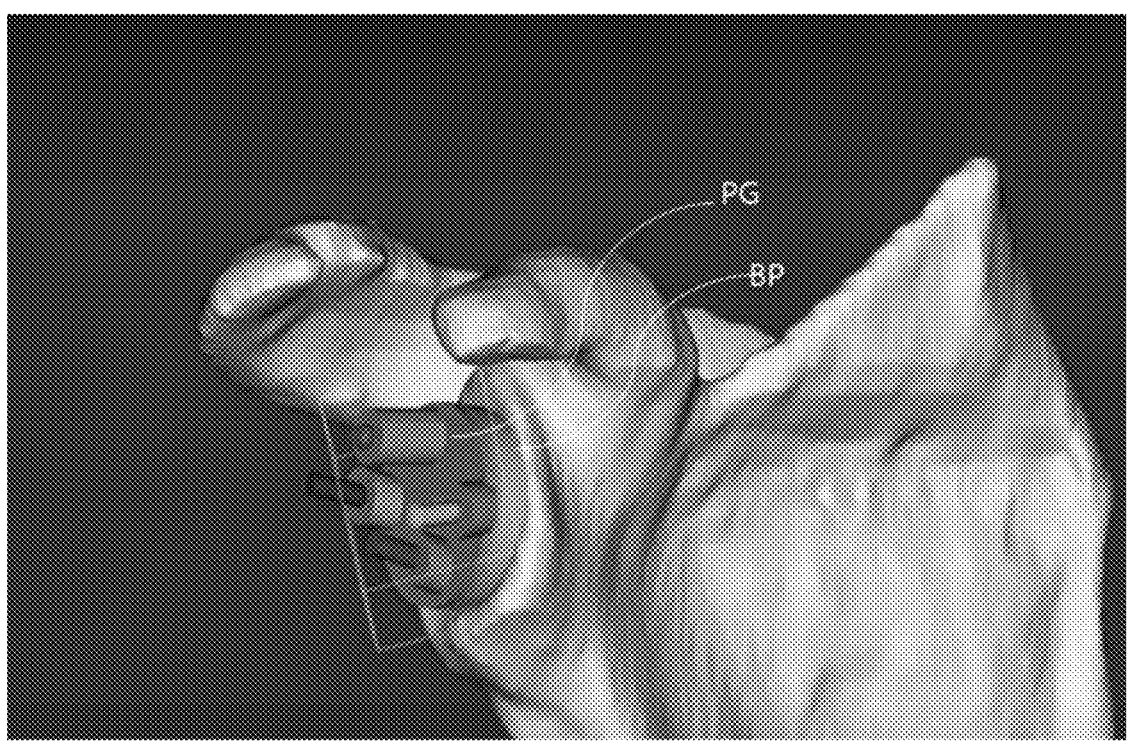

Sequentially, FIG. 7B is a screen showing a peripheral screw guidance (a peripheral guidance) that facilitates installation of peripheral screws on the base plate BP according to an embodiment.

Figure 8:
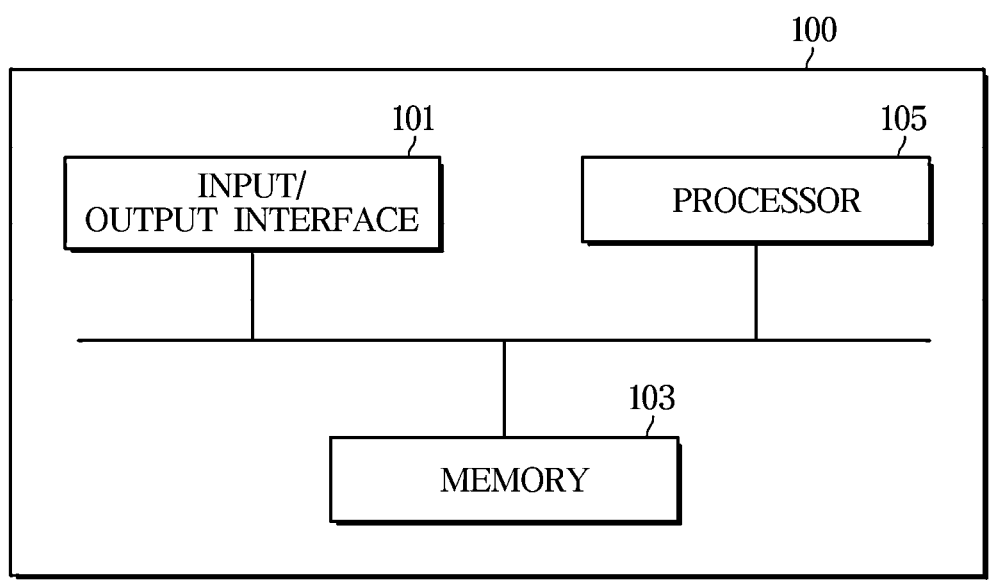
FIG. 8 is a block diagram illustrating a structure of a design apparatus according to an embodiment.

FIG. 8 is a block diagram illustrating the structure of a design apparatus according to an embodiment.

According to the embodiment, the electronic apparatus 100 may include an input/output interface 101, a memory 103, and a processor 105. In the embodiment, the electronic apparatus 100 may be connected to an external server or database through a transceiver or communication interface, and exchange data.

The processor 105 may perform at least one method described above with reference to FIGS. 1 to 7B. The memory 103 may store information for performing at least one method described above with reference to FIGS. 1 to 7B. The memory 103 may be a volatile memory or a non-volatile memory.

The processor 105 may control the electronic apparatus 100 to execute programs and provide information. Program code executed by the processor 105 may be stored in the memory 103.

The processor 105 may, in connection with the memory 103, specify a skeletal image on which a base plate is to be installed, determine the position and direction of a center point CP of the base plate, visually display the determined position and direction in 3D dimensions for the user to arbitrarily adjust the determined position and direction, store information about the angle adjusted by the user to generate a center point guidance, calculate the angles of peripheral screws according to the determined position and direction of the center point, and generate a peripheral screw guidance at the calculated peripheral screw angles and display the peripheral screw guidance separately or to be overlaid on the skeletal image.

The electronic apparatus 100 shown in FIG. 8 includes only components related to the disclosed embodiment. Accordingly, those skilled in the art may understand that other general-purpose components may be included in addition to the components shown in FIG. 8.

As an example, the electronic apparatus 100 shown in FIG. 8 may be a server of a system for providing a collaborative service between a user and an operator, in 3D modeling for designing or producing a patient-specific body model or a patient-specific medical device in relation to a medical service.

In this case, the system for providing a collaborative service may further include a plurality of operator apparatuses or user apparatuses similar to the electronic apparatus 100 shown in FIG. 8, as well as the server. Therefore, according to an embodiment, the system for providing a collaborative service may further include a network for supporting information transmission and reception between at least a part of the operator apparatuses or user apparatuses for a collaborative service between users and operators.

The electronic apparatus 100 according to the above embodiments may include a processor, a memory for storing and executing program data, a permanent storage such as a disk drive, and a user interface device, such as a communication port for communicating with an external device, a touch panel, a key, a button, and the like. Methods implemented with software modules or algorithms may be stored on a computer readable recording medium as computer readable codes or program instructions executable on the processor. Here, the computer-readable recording media include a magnetic storage medium (e. g., a read-only memory (ROM), a random-access memory (RAM), a floppy disk, a hard disk, and the like), an optical readable medium (e. g., a compact disk (CD)-ROM, a digital versatile disk (DVD), etc.) and other recording media. The computer-readable recording medium may be distributed over computer systems connected through a network such that computer readable codes may be stored and executed in a distributed manner. The medium may be readable by a computer, stored in a memory, and executable in a processor.

The embodiments may be represented by functional block configurations and various processing operations. These functional blocks may be implemented with any number of hardware and/or software configurations that perform particular functions. For example, the embodiments may adopt integrated circuit configurations such as memory, processing, logic, look-up tables, etc., which may perform various functions by control of one or more microprocessors or by other control devices. Similar to the way in which components may be implemented in software programming or software components, the present embodiments may be implemented in a variety of ways, including C, C++, Java, an assembler, python, and the like. Functional aspects may be implemented with algorithms running on one or more processors. In addition, the present embodiment may employ conventional techniques for electronic environment setting, signal processing, and/or data processing. Terms such as "mechanism", "element", "means", "configuration" may be used broadly and are not limited to mechanical and physical configurations. The term may include the meaning of a series of routines of software in conjunction with a processor or the like.

As is apparent from the above, the method disclosed herein is implement to provide a guidance that may allow a patient-specific fixation angle to be calculated such that an implant is correctly installed in a patient-specific position in an artificial joint replacement surgery, thereby reducing risks in an actual replacement surgery.

In addition, the method disclosed herein is implement to design a guidance that may be intuitively identified in a glenoid, thereby controlling errors occurring due to environmental differences between a virtual three-dimensional space and a real space.

The effects of the present invention are not limited to those described above, and other effects not described above is clearly understood by those skilled in the art from the above detailed description.

The above-described embodiments are merely examples and other embodiments may be implemented within the scope of the claims described below.

What is claimed is:

1. A method of designing a guidance specific to a patient, the method comprising:
   specifying, by a processor, a first skeletal image plane in which a base plate is to be installed on a skeleton of a patient in which an affected area is located;
   displaying, by the processor, a normal vector N of the first skeletal image plane together with the skeleton of the patient in three dimensions (3D);
   displaying, by the processor, an intersection of the normal vector and the first skeletal image plane such that an operator arbitrarily moves the intersection or rotates the normal vector based on the intersection to determine a direction of a center pin;
   displaying, by the processor, a screen in which the base plate is installed according to a position (a center point) and direction of the center pin determined by the operator; and calculating, by the processor, a rotation angle and a depth of peripheral screws to be installed on the base plate,
wherein the calculating, by the processor, of the rotation angle and the depth of the peripheral screws to be installed on the base plate includes:
specifying, by the operator, points p of the plurality of peripheral screws to be installed on the base plate; and
rotating, by the processor, the plurality of peripheral screws in an arbitrary range of rotation angles at the specified points of the plurality of peripheral screws, and
wherein the rotating, by the processor, of the plurality of peripheral screws in an arbitrary range of rotation angles at the specified points of the plurality of peripheral screws further includes:
installing, by the processor, the plurality of peripheral screws in a same direction as the center pin at the specified points p of the plurality of peripheral screws;
calculating, by the processor, a distance d from the point of the peripheral screw to an intersection between a ray L in the same direction as the center pin and a triangle formed by arbitrary three points on the skeleton of the patient;
repeatedly calculating, by the processor, the distance d with respect to a preset range of rotation angles ($r_x$, $r_y$) of the ray L; and
based on the rotation angle ($r_x$, $r_y$) at which a maximum distance d is calculated from the repeatedly calculated distances, determining a final rotation angle and a depth corresponding to the maximum distance d, of the peripheral screw.

2. The method of claim 1, wherein the specifying, by the processor, of the first skeletal image plane in which the base plate is to be installed on the skeleton of the patient in which the affected area is located includes:
upon selecting, by the operator, at least four outermost points p1 to p4 on one side of the skeleton of the patient in which the base plate is to be installed, calculating, by the processor, a center point that is a crossing point of the outermost points, or arbitrarily determining a center point; and
calculating, by the processor, a normal vector from the center point.

3. The method of claim 2, wherein the displaying, by the processor, of the intersection of the normal vector and the first skeletal image plane such that the operator arbitrarily moves the intersection or rotates the normal vector based on the intersection to determine the direction of the center pin includes:
moving, by the operator, the center point in an arbitrary direction; or
adjusting, by the operator, a rotation angle of the center pin.

4. The method of claim 1, wherein the displaying, by the processor, of the screen in which the base plate is installed according to the position and direction of the center pin determined by the operator includes:
displaying, by the processor, at least one base plate on a screen; and
displaying, by the processor, a base plate selected by the operator among the at least one base plate to be overlaid on the first skeleton image plane in alignment with the center point.

5. The method of claim 1, further comprising:
generating, by the processor, a center pin guidance of the center pin generated with respect to the first skeleton image plane; and
displaying, by the processor, the center pin guidance to be overlaid on the skeleton, or displaying only the center pin guidance.

6. The method of claim 5, wherein the generating, by the processor, of the center pin guidance of the center pin generated with respect to the first skeleton image plane includes:
setting, by the operator, a bridge position on the first skeletal image plane of the center pin;
generating, by the processor, a bridge at the set bridge position; and
finally generating, by the processor, the center pin guidance including the bridge and displaying the finally generated center pin guidance.

7. The method of claim 1, further comprising
generating, by the processor, a peripheral screw guidance based on a rotation angle and a depth of a peripheral screw to be installed on the base plate.

8. The method of claim 7, wherein the generating, by the processor, of the peripheral screw guidance based on the rotation angle and the depth of the peripheral screw to be installed on the base plate includes
installing the peripheral screw guidance on an upper side of the base plate and displaying the installed peripheral screw guidance.

* * * * *